United States Patent [19]

Alongi et al.

[11] Patent Number: 4,736,836

[45] Date of Patent: Apr. 12, 1988

[54] INTRAOCULAR LENS PACKAGE

[76] Inventors: Salvatore A. Alongi; William R. Carleton, both of 5743 Thornwood Dr., Goleta, Calif. 93117

[21] Appl. No.: 9,895

[22] Filed: Feb. 2, 1987

[51] Int. Cl.[4] ............................................. B65D 81/24
[52] U.S. Cl. .................................... 206/5.1; 206/438; 623/6
[58] Field of Search .................... 128/303 R; 206/5.1, 206/438, 439, 210, 525; 356/246; 623/4, 6

[56] References Cited

U.S. PATENT DOCUMENTS

| | | | |
|---|---|---|---|
| 4,113,088 | 9/1978 | Binkhorst | 356/246 |
| 4,269,307 | 5/1981 | Lahaye | 206/5.1 |
| 4,402,396 | 9/1983 | Graham | 206/5.1 |
| 4,615,703 | 10/1986 | Callahan | 206/5.1 |

Primary Examiner—Jimmy G. Foster
Attorney, Agent, or Firm—Hugh D. Jaeger

[57] ABSTRACT

Intraocular lens package for packing, shipping or storage of intraocular lenses including a base and a configured cavity for the containment of an IOL and a lens retainer cap fitting over and about the configured cavity to contain the IOL within a seat. The haptics rest on ramped surfaces adjacent to a centralized lens cavity which is supported by semi-tubular struts. A lens retainer cap positions on beveled support posts to form an upper surface of the lens cavity. Lens haptics fit between the support posts to prevent rotational movement of the IOL in the lens package. Tightening flanges in the lens retainer cap engage in ramped catches in the inner perimeter of the configured cavity to secure the lens retainer cap to the configured cavity. Differently configured cavity interiors accept different configurations of posterior and anterior chamber lenses.

7 Claims, 10 Drawing Sheets

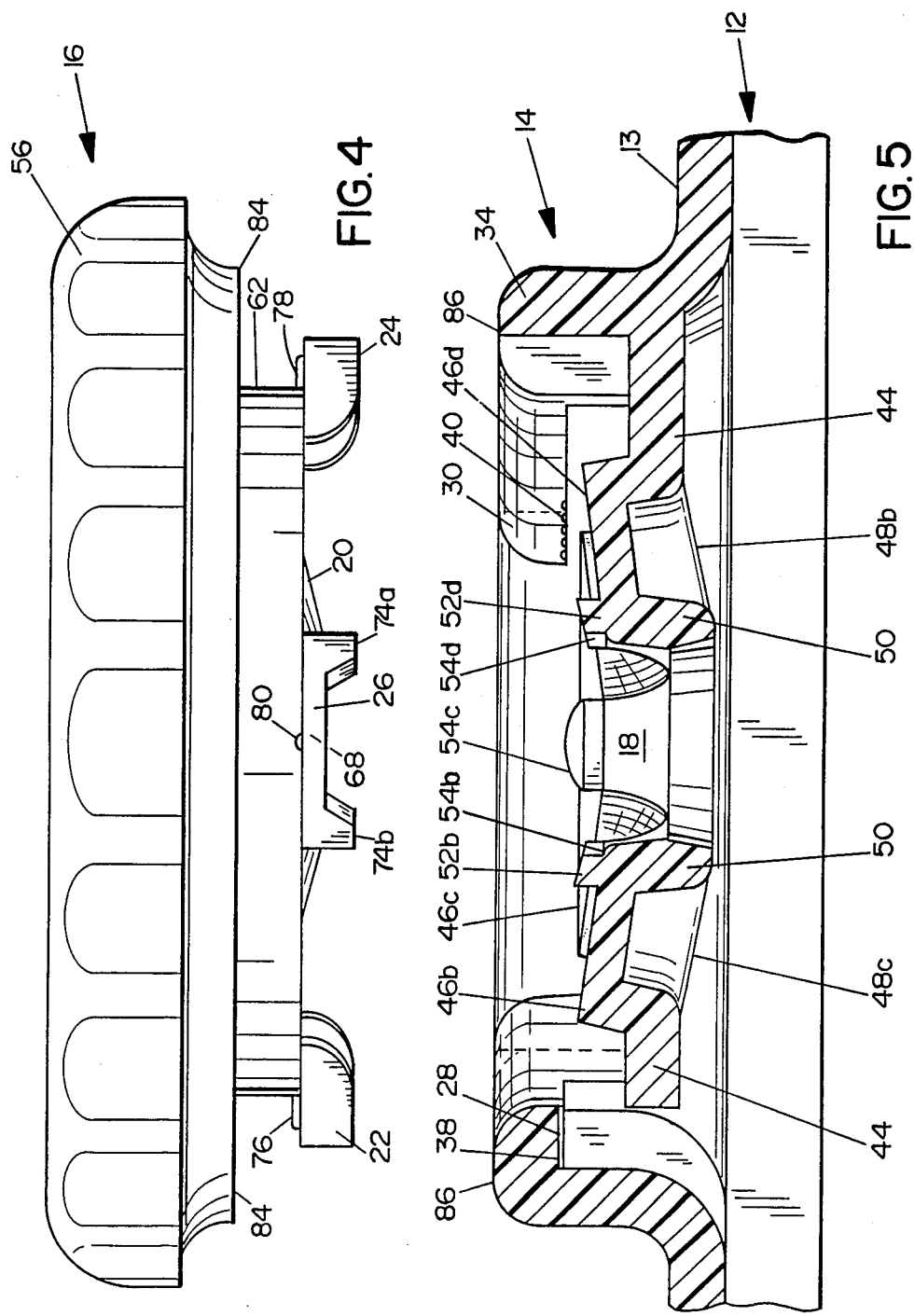

INTRAOCULAR LENS PACKAGE

BACKGROUND OF THE INVENTION

1. Field of the Invention

The present invention pertains to an IOL lens package, and more particularly, pertains to packages for containment of either anterior or posterior chamber lenses enclosed in a cavity or chamber and secured within by a screw-on cap.

2. Description of the Prior Art

Representative prior art intraocular lens packages include U.S. Pat. Nos. 4,173,281; 4,269,307; and 4,402,396.

The present invention provides a new and novel lens package structure of the prior art.

SUMMARY OF THE INVENTION

The general purpose of the present invention is to provide lens carriage and storage packages which can contain different configured interior cavities for the safe containment and carriage of intraocular lenses, such as anterior chamber lenses and posterior chamber lenses, including vaulted or non vaulted haptics. Lenses can be plano-convex, bi-convex, concave-convex and other like shapes, and the loops of the intraocular lens can be either open loops or closed loops of one or more in number.

According to one embodiment of the present invention there is provided an intraocular lens positioned in a lens cavity including a segmented seating surface and a configured central ring. Semi-tubular struts extend outwardly from the raised annular rim and lens cavity to a washer shaped circular support member which is interior to a raised annular rim. Haptics position upon a ramped segmented disc surrounding the lens cavity. Vertical support posts limit lens movement laterally, and the loops position between pairs of the support loops to preclude rotational movement within a central cavity. The support posts are also stops for a conical surface of the lens retainer cap. A lens retainer cap, including a shallow conically shaped disc positions and fastens over and about the cavity with peripheral flanges engaging ramped notched surfaces integral to a raised annular ring. Alternatively, the interior chamber configuration can be configured differently to accommodate differently styled lenses.

One significant aspect and feature of the present invention is a lens package suitable to optic inspection by the surgeon without removal of the optic from the protective package.

Another aspect and significant feature of the present invention is a screw on containment cap which senses the optic within the lens chamber.

Another aspect and significant feature of the present invention is a lens chamber offering minimal contact with the enclosed optic.

Another aspect and significant feature of the present invention is an option of differently configured lens supports and chambers for differently configured lenses.

Having thus described one embodiment of the present invention it is a principal objective hereof to provide an IOL lens package for the carriage and protection of IOL's utilizing a screw-on cap and configured cavity, that configured cavity assuming different support assemblies for differently styled lenses.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein:

FIG. 4 illustrates a side view of the lens retainer cap;

FIG. 5 illustrates a cross-sectional side view of the configured lens cavity;

DESCRIPTION OF THE PREFERRED EMBODIMENTS

Figure 1:
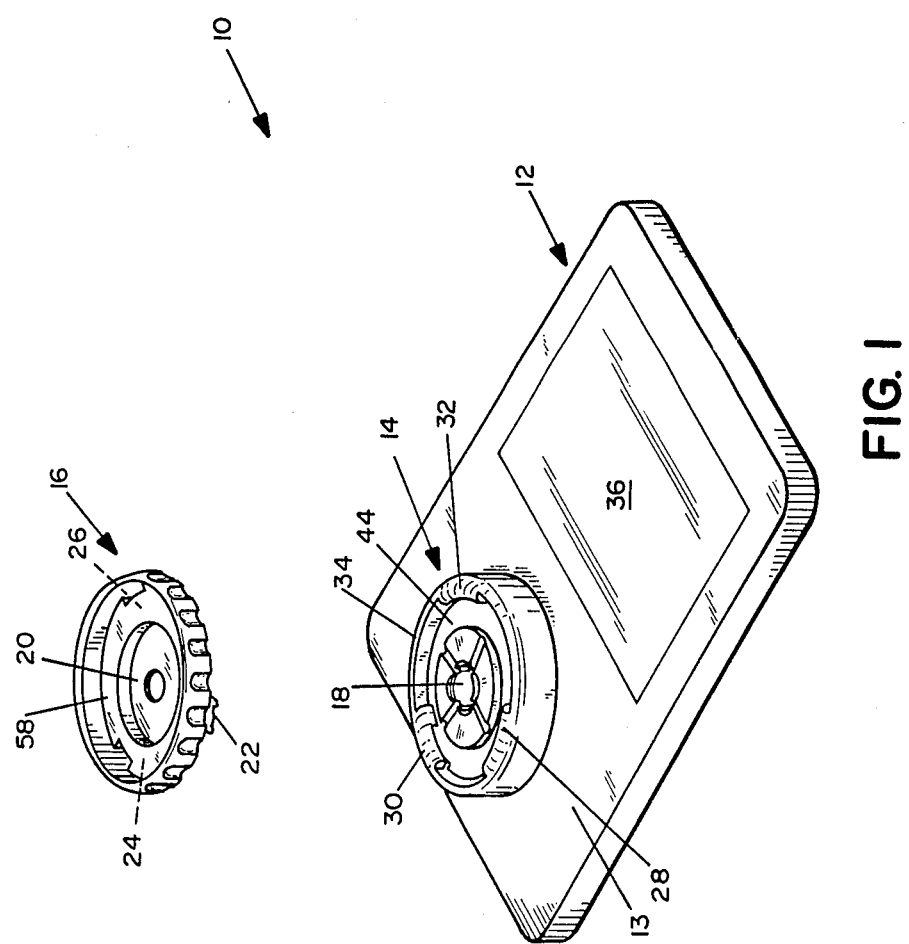
FIG. 1 illustrates a perspective view of an intraocular lens package including a base, a configured cavity and a lens retainer cap.

FIG. 1 illustrates a perspective view of a posterior intraocular lens package 10, the present invention including a base 12, a configured cavity 14 positioned on the upper surface 13 of the base 12 and a lens retainer cap 16 which secures over and about the configured cavity 14 to retain and contain a posterior chamber intraocular lens as later described in detail. A lens is placed in and rests in the lens cavity 18 and is secured in the cavity by a almost flat conically shaped disc 20 integral to the lens retainer cap 16. Flanges 22-26 in the lens retainer cap 16 engage and secure within corresponding ramped catches 28, 30 and 32 integral to raised annular rim 34 to secure the lens retainer cap 16 to the configured cavity 14 and retain an IOL within the lens cavity 18 as later described in detail. A rectangular data placard surface 36 positions on the upper surface of the base 12.

Figure 2:
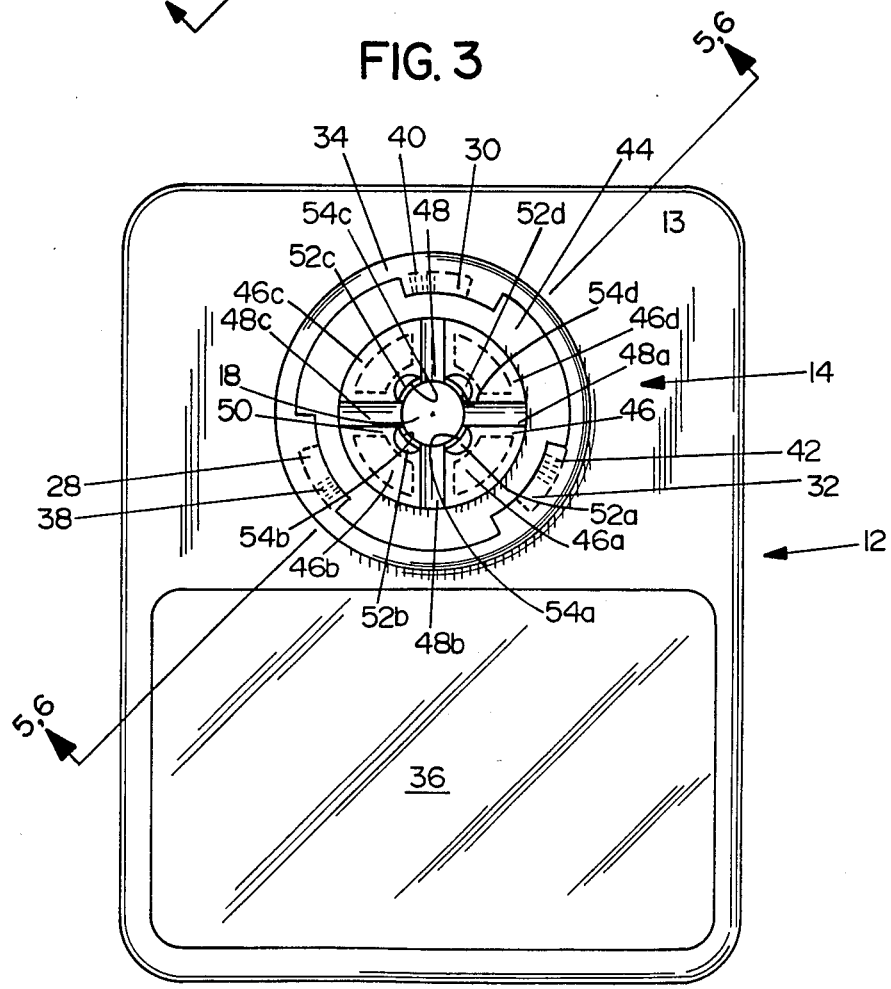
FIG. 2 illustrates a top view of the configured cavity and base.
Figure 6:
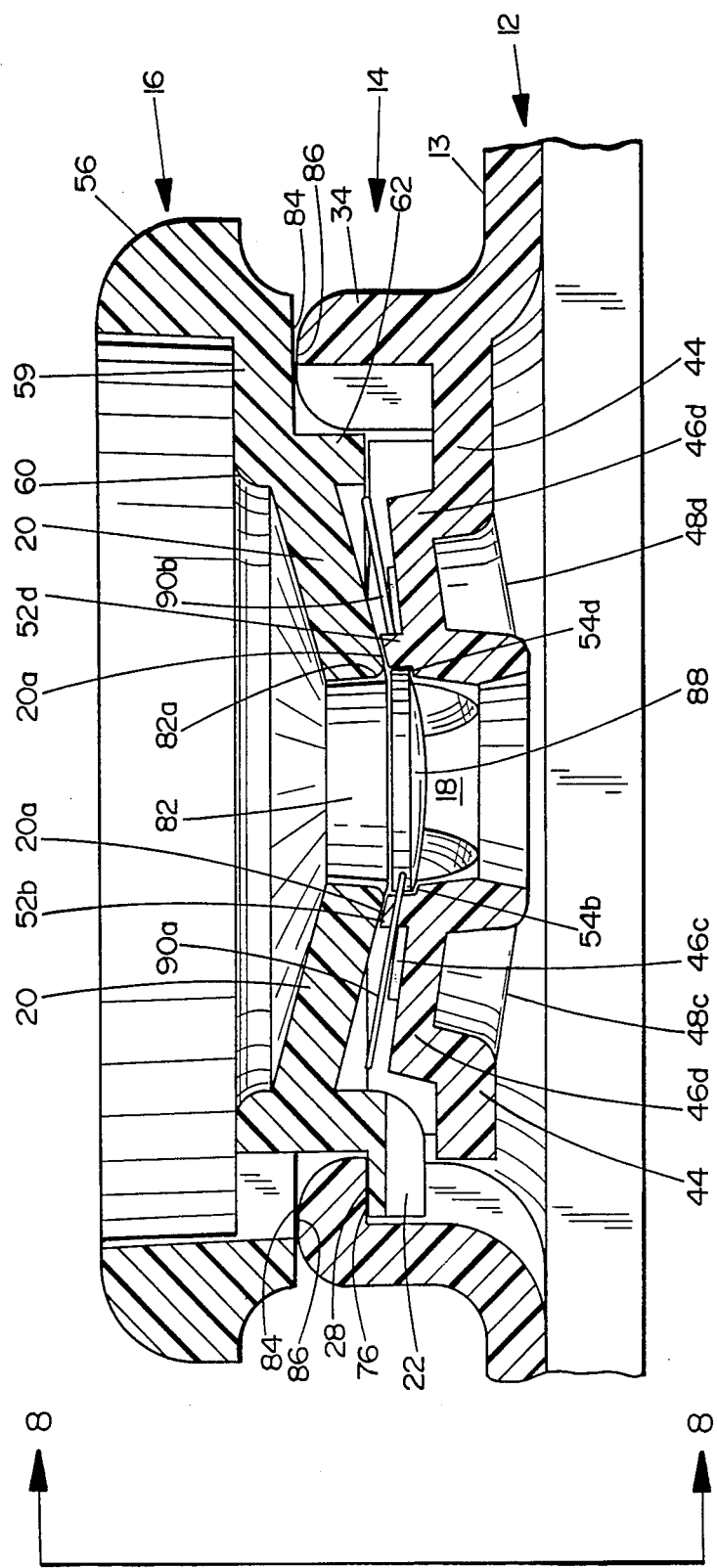
FIG. 6 illustrates a cross-sectional view of a lens retainer cap engaged over and about the configured lens cavity and retaining an IOL within the lens cavity.

FIG. 2 illustrates a top view of the configured cavity 14 positioned on an upper surface 13 of the base 12 where all numerals correspond to those elements previously described. Ramped catches 28, 30 and 32 position on the inner side walls of the raised annular rim 34. The underneath sides of the catches are ramped upwardly each containing a series of notches 38, 40 and 42 positioned on the ramped surface. A circular support member 44 much resembling a washer positions above the plane of the base 12 and within the raised annular rim 34 and extends inwardly from the inner walls of the raised annular rim 34 to support the outer portions of a segmented disc 46 including sections 46a, 46b, 46c and 46d. Semi-tubular struts 48a, 48b, 48c and 48d extend inwardly from the inner radius of the circular support member 44 and between respective segmented disc 46 sections to support the edges of the segmented disc 46 and to support a central configured rim 50 as also illustrated in FIG. 5. The upper surfaces of the segmented disc 46 are ramped and slope downwardly towards the center and inwardly towards the lens cavity 18 to accommodate lens loops as described later in detail. Beveled top rounded support posts 52a, 52b, 52c and 52d position vertically on the inner portion of the segmented disc sections 46a–46d and are extensions of the upper portion of the central configured rim 50. Inwardly and downwardly beveled and radiused support seats 54a, 54b, 54c and 54d position on the inner surface and just below the top of the support post 52a–52d to support an intraocular lens in the lens cavity 18 as also illustrated in FIGS. 5 and 6.

Figure 3:
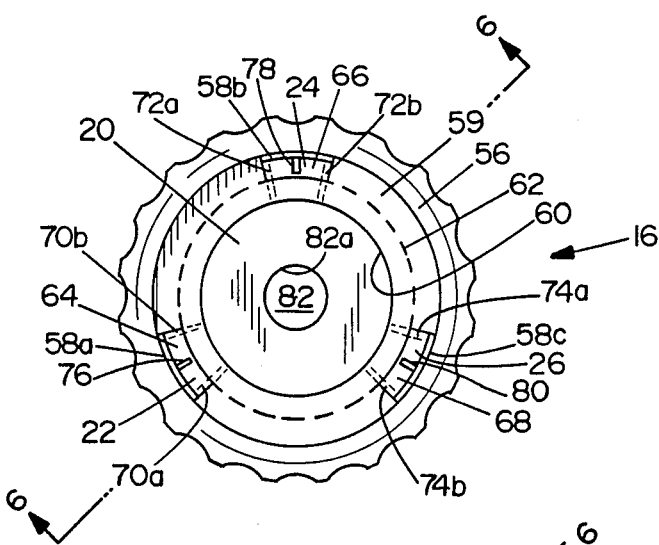
FIG. 3 illustrates a top view of the lens retainer cap.

FIG. 3 illustrates a top view of the lens retainer cap 16 where all numerals correspond to those elements previously described. The retainer cap includes a circular raised fluted gripping rim 56 for actuation of the lens retainer cap 16 over and about the configured cavity 14. A circular support member 58 somewhat resembling a washer shape and having a finite width extends inwardly from the lower portion of the circular gripping rim 56 to form an inner circular edge 60. An annular ring 62 extends downwardly from the inner circular edge 60. Flanges 22–26 extend downwardly and outwardly from the lower suface of the annular ring 62 to subsequently engage with the ramped catches 28, 30 and 32 for securement of the lens retainer cap 16 to the configured cavity 14. Three rectangular like mold processing holes 58a, 58b and 58c position over flanges 22–26. Flanges 22–26 include flange bars 64, 66 and 68 and flange support struts 70a, 70b, 72a, 72b, 74a and 74b respectively. Locking teeth 76, 78 and 80 position on the upper surface of flanges 22–26 for engagement with series of notches 38–42 in ramped catches 28–32. A shallow conically shaped member 20 extends inwardly and downwardly toward the center and contains a hole 82 with a rounded smooth lower smoothed lower edge 82a. Rounded edge 82a provides a contact surface for high G-loadings if required to retain an IOL between the lens retainer cap 16 and the lens cavity 18 as illustrated in FIG. 6 but does not normally come in contact with the IOL.

FIG. 4 illustrates a side view of the lens retainer cap where all numerals correspond to those elements previously described. Lens retainer cap 16 is positioned above the configured cavity 14 prior to IOL insertion and is rotated for sake of clarity of illustration and symmetry showing flange positioning. Shown in particular is the flat circular mating surface 84 adjacent to the annular ring 62 and the placement of locking tooth 80 on flange 26, as well as other corresponding locking teeth and flanges.

FIG. 5 illustrates a cross-sectional side section view of the configured cavity 14 taken along line 5—5 of FIG. 2 where all numerals correspond to those elements previously described. Shown in particular is the lens cavity 18 and an end-on view of the ramped catch 28. A cavity mating surface 86 assuming the shape of a circle is formed by the upper edge of the raised annular rim 34 and mates with plat circular mating surface 84 of the lens retainer cap 16.

Figure 7:
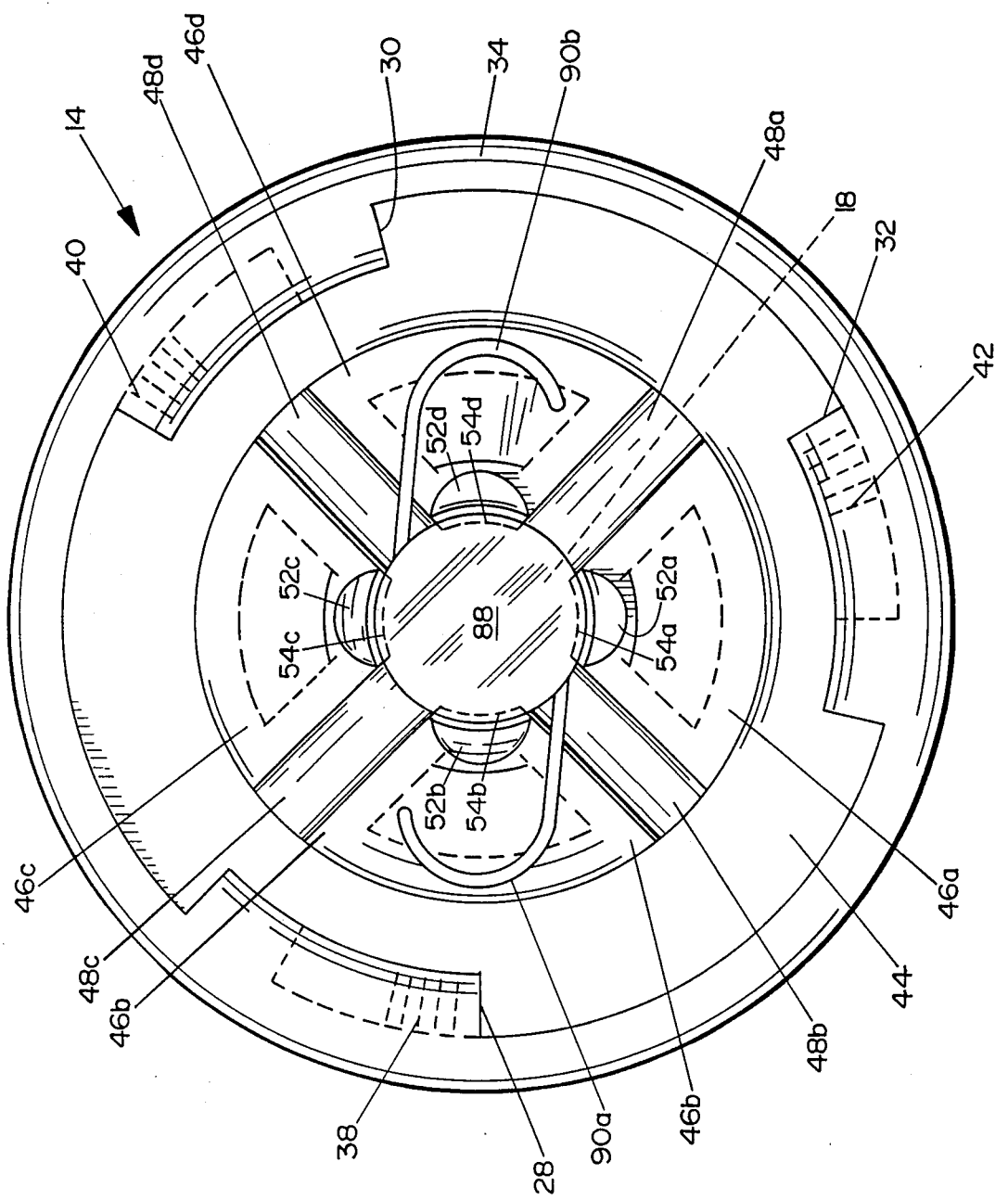
FIG. 7 illustrates a posterior IOL in the lens chamber in the configured cavity.

FIG. 6 best illustrates the mode of operation and illustrates a view in cross section of the intraocular lens' package 10 with the lens retainer cap 16 engaged over and about the configured cavity 14 and retaining an IOL 88 within lens cavity 18 where all numerals correspond to those elements previously described. An IOL 88 engages and rests on and in appropriately sized beveled and radiused support seats 54a–54d and within lens cavity 18 as also illustrated in FIG. 7. Vaulted IOL loops 90a and 90b position as illustrated over portions of the segmented disc 46. The exact segments of which they overlay are determined by a plurality of orientation schemes of the lens and its placement in the lens cavity 18 and is not construed to be limiting in nature. The surface of the shallow conically shaped disc 20 conforms to the vaulted IOL loops 90a and 90b and an inner lower annular surface 20a of the conically shaped disc 20 adjacent to hole 82 positions touching the upper surfaces of the support posts 52a–52d to contain the IOL 88 in the lens cavity 18. The rounded smooth lower edge 82a at the edge of hole 82 retains and comes in close proximity to but does not engage in contact with the planar surface or any other surface of the IOL 88.

For purposes of illustration lens retainer cap 16 is shown with locking flange 22 engaged within ramped catch 28 as would other like locking flanges within their respective locking catches. The lens retainer cap 16 is turned clockwise to engage locking flange 22 and like flanges fully into the ramped catch 28 and respective catches. The locking tooth 76 of flange 22 engages against the notched ramped under surface of ramped catch 28 utilizing spring like qualities of the flange 22 as it is depressed downwardly by the under surface of the ramped catch 28 to press and engage the locking tooth 76 into a notch of notch series 38 and rotationally securing the lens retainer cap 16 in a fixed position over and above the configured cavity 14. Locking flanges 22–26 operate in unison within respective ramped catches 28–32 to secure the plat circular mating surface 84 to the cavity mating surface 86 securing the IOL 88 as illustrated within the lens cavity 18.

FIG. 7 illustrates a posterior IOL 88 within lens cavity 18 of configured cavity 14 where all numerals correspond to those previously described. IOL 88 rests in the beveled and radiused support seats 54a–54d located in beveled top rounded support posts 52a–52d. As illustrated vaulted IOL loop 90a positions between support post 52a and 52b and in a similar fashion vaulted IOL loop 90b positions between support posts 52c and 52d. Rotational movement of the IOL 88 is limited by the spacing between any two adjacent beveled top rounded support posts 52 between which the vaulted IOL loops 90a–90b are positioned. Of course the vaulted IOL loops 90a and 90b can be positioned between other adjacent pairs of beveled top rounded support posts 52 and is not construed to be limiting as to the number of support posts utilized. Vaulted IOL loops 90a and 90b ends can position above opposing pairs of segmented disc 46 as illustrated in FIG. 7 on sections 46b and 46d and below conically shaped disc surface 20 of the lens retainer cap 16

Figure 8:
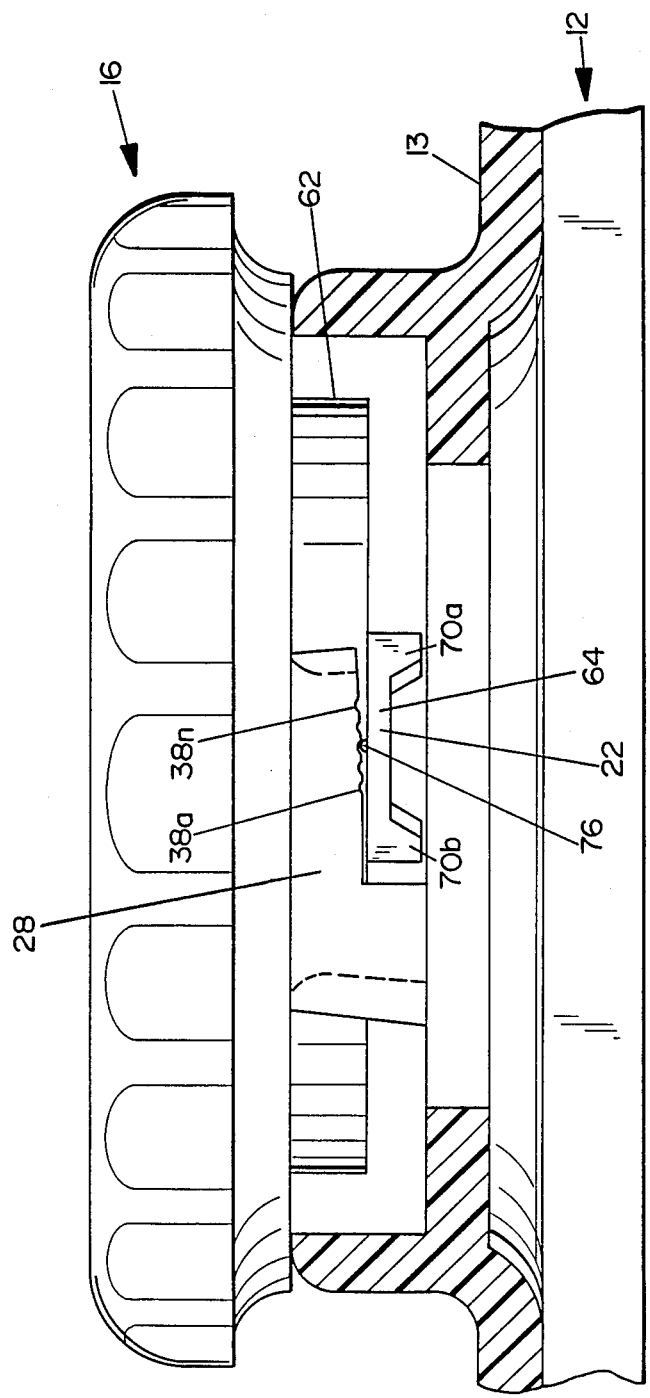
FIG. 8 illustrates a cutaway view of a locking flange engaged in a ramped catch.

FIG. 8 illustrates a cutaway view of a locking flange engaging a ramped catch along line 8—8 of FIG. 6 where all numerals correspond to those previously described. Ramped catch 28 is shown in engagement with flange 22 where the near side of the raised anular rim 34 has been cut away exposing and leaving the ramped catch 28 exposed. For brevity and clarity of illustration other notches and flanges are not illustrated in FIG. 8. As the lens retainer cap 16 is turned clockwise, locking tooth 76 and flange 22 are sprung downwardly against the notched ramped surface of the ramped catch 28 and against the inherent spring qualities of flange 22 and flange bar 64 to provide a pressure fit of the locking tooth 76 in one of the notches of notch series 38a-38n thus locking the lens retainer cap 16 and preventing it from working loose by action of outside forces such as vibration.

Figure 9:
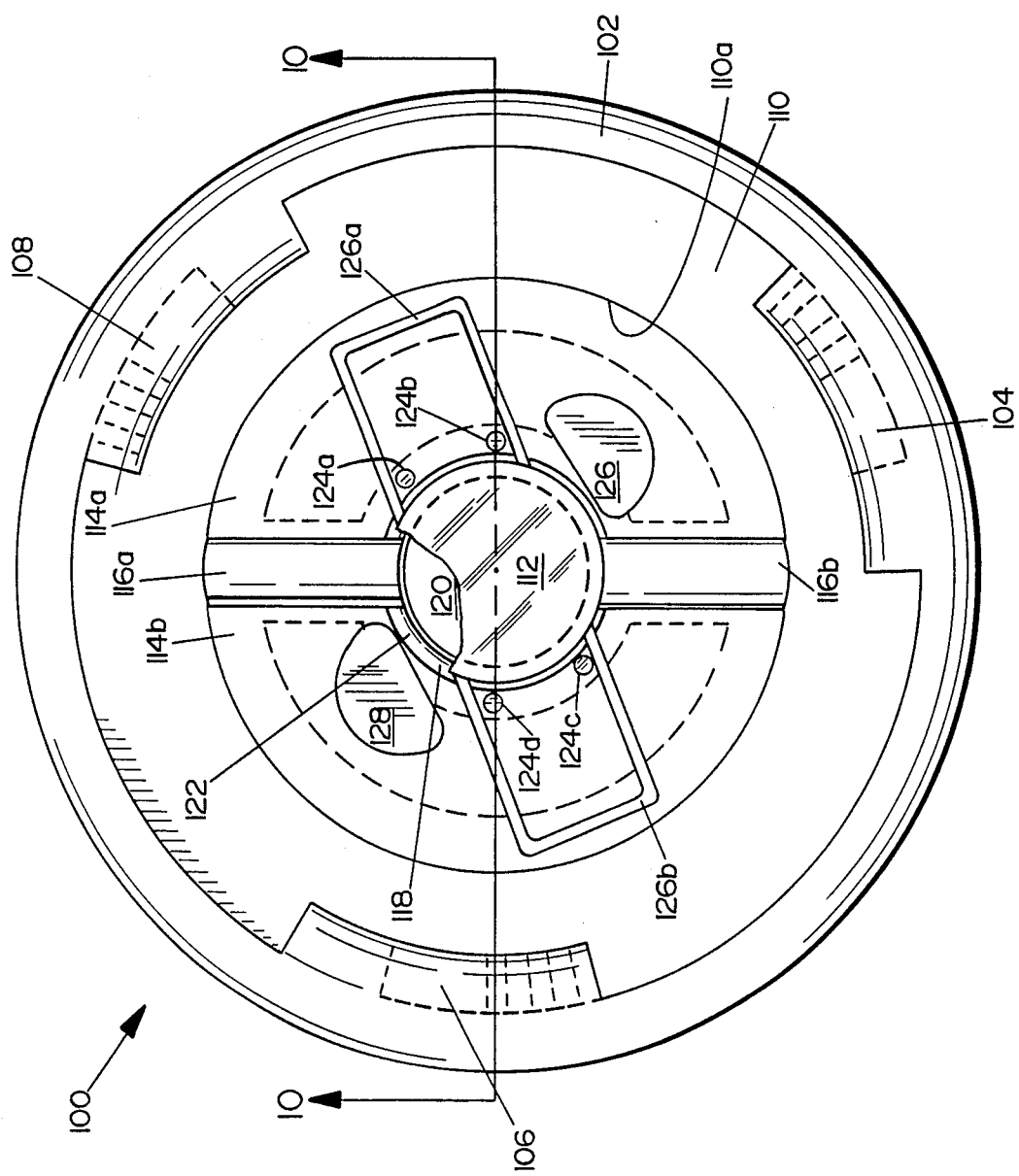
FIG. 9 illustrates a top view of an alternative embodiment of an intraocular lens cavity containing an anterior chamber IOL.

FIG. 9 illustrates an alternative embodiment top view of configured cavity 100 for an anterior chamber lens where all numerals correspond to those previously described. Raised annular rim 102 being similar to raised rim 34, ramped notched catches 104-108 correspond and are similar to ramped notched catches 28-32 and circular support member 110 corresponds to circular support 44. Lens retainer cap 16 functions in a similar manner and fits over and about the configured cavity 100 as in previously described figures. Portions of the configured cavity 100 inboard of circular support member 110 form a support for an anterior chamber IOL 112 as illustrated in a cutaway view of the lens where the segmented disc halves 114a and 114b position centrally within and are ramped downwardly and outwardly from the center to the inner radius portion 110a of circular support member 110. Semi-tubular struts 116a and 116b position between the circular support member 110 and the configured central ring 118 and support the edges of the sloping segmented disc halves 114a and 114b therebetween. A lens cavity 120 is formed by the upper regions of the configured central ring 118 including a circular radiused support seat 122.

Pairs of vertical beveled haptic locating posts 124a-124b and 124c-124d position as illustrated on the surfaces of segmented disc halves 114a and 114b and above the upper edge of the configured central ring 118. The upper beveled surface of haptic locating posts 124a-124d function as stops as do beveled top rounded sipport posts 52a-52d for the shallow conically shaped disc 20 of lens retainer cap 16. Semi-elliptical flat topped configured IOL positioner members 126 and 128 position on the surfaces of segmented disc halves 114a and 114b respectively. The flat side wall portion of configured IOL positioner members 126 and 128 adjacent to the configured central ring 118 position the anterior cavity IOL 112 within the lens chamber 120. Haptics 126a and 126b position over haptic locating posts 124a-124b and 124c-124d respectively to preclude rotation of the optic of the anterior chamber IOL 112 about its vertical axis when engaged in the lens package. Haptics 126a and 126b position over the downwardly sloping surfaces of segmented disc halves 114a and 114b.

Figure 10:
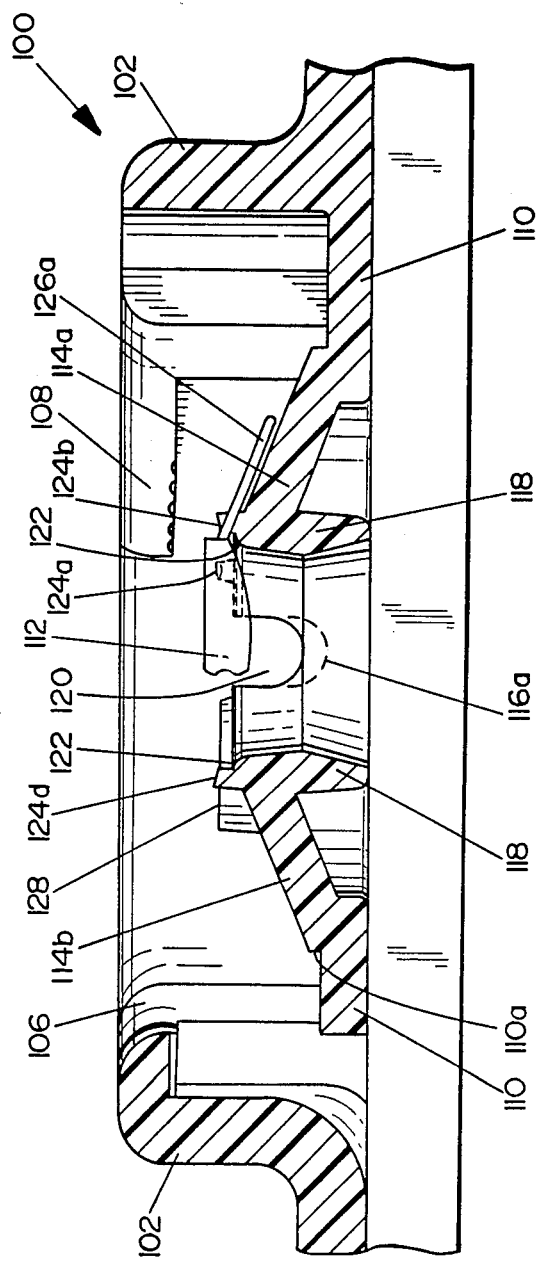
FIG. 10 illustrates a sectional view of the alternative embodiment of an anterior chamber IOL within the lens chamber cavity taken along line 10—10 of FIG. 9.

FIG. 10 illustrates a sectional view of the anterior chamber lens configured cavity 100 taken along line 10—10 of FIG. 9 where all numerals correspond to those previously described. Shown in particular is a portion of an anterior chamber lens 112 on the circular radiused support seat 122 of lens cavity 120 and the configuration of the downwardly ramped segmented disc halves 114a and 114b supporting the configured central ring 118.

Figure 11:
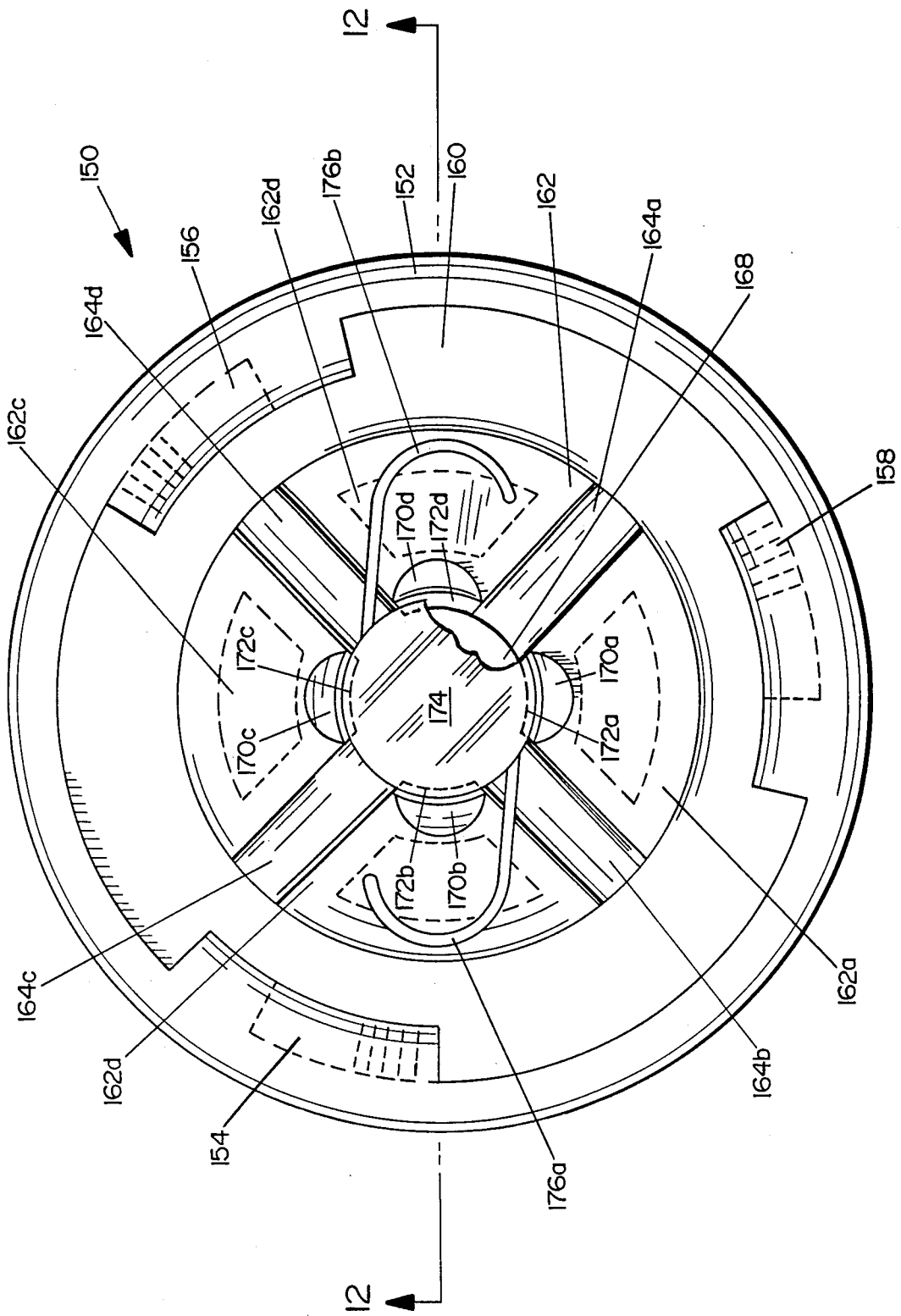
FIG. 11 illustrates a top view of an alternative embodiment of a non-vaulted loop IOL within the lens chamber in a configured cavity; and, FIG. 12 illustrates a sectional view of an alternative embodiment of FIG. 11 of a non-vaulted IOL within the lens chamber taken along line 12—12 of FIG. 11.

FIG. 11 illustrates an alternative embodiment top view of a configured cavity 150 for an intraocular lens having no haptic vaulting, where all numerals correspond to those previously described. Raised rim 152 is similar and corresponds to raised annular rim 34 and ramped notched catches 154-158, and are similar and correspond to ramped catches 28-32. Lens retainer cap 16 functions in a similar manner and fits over and about the configured cavity 150 as in previously described figures.

Figure 12:
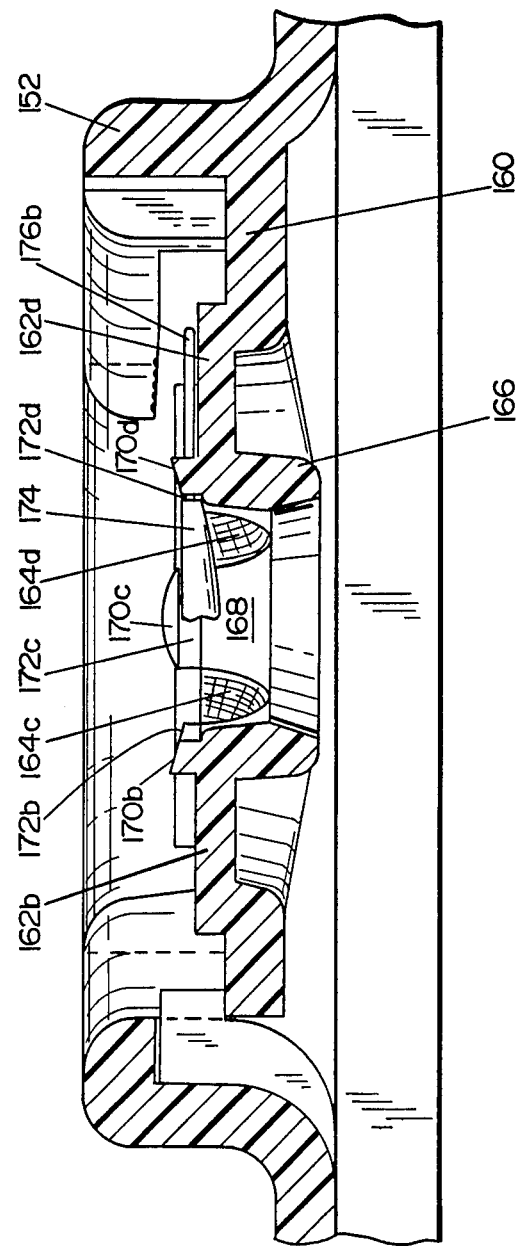

A circular support member 160 much resembling a washer positions above the plane of the base 12 and within the raised annular rim 152 and extends inwardly from the inner walls of the raised rim 152 to support the outer portions of a segmented disc 162 including sections 162a, 162b, 162c and 162d. Semi-tubular struts 164a, 164b, 164c and 164d extend inwardly from the inner radius of the circular support member 160 and between respective segmented disc 162 sections to support the edges of the segmented disc 162 and to support a central configured ring 166 as also illustrated in FIG. 12. The upper surfaces of the segmented disc 162 are horizontal and extend from the inner radius of the circular support member 160 towards the lens cavity 168 to accommodate non-vaulted lens loops as described later in detail. Beveled top rounded support posts 170a, 170b, 170c and 170d position vertically on the inner portion of the segmented disc sections 162a-162d and are extensions of the upper portion of the central configured ring 166 as shown in FIG. 12. Inwardly and downwardly beveled and radiused support seats 172a, 172b, 172c and 172d position on the inner surface and just below the top of the support post 170a-170d to support an intraocular lens 174 in the lens cavity 168 as also illustrated in FIG. 12.

FIG. 12 illustrates a cross-section view of FIG. 11 taken along line 12—12, where all numerals correspond to those elements previously described. Shown in particular is a portion of a unvaulted intraocular lens 174 resting on radiused appropriately sized support seats 172a-172d and within lens cavity 168, as also illustrated in FIG. 11. Straight non-vaulted loops 176a-176b position as illustrated over portions of the segmented disc 162, but may overlay other segments as determined by a plurality of orientation schemes of the lens and its placement in the lens cavity 168. The surface of the shallow conically shaped disc 20 positions as previously described touching the upper surfaces of support posts 170a-170d to contain the non-vaulted loop 174 in the lens chamber 168. Lens 174 is illustrated as plano-convex, but other shaped lens optics such as bi-convex or meniscus shaped lenses may be accommodated within lens chamber 168 with various and minor modifications to the support structures and is not construed to be limiting in scope or nature of the invention.

Various modifications can be made to the present invention without departing from the apparent scope thereof.

We claim:

1. An intraocular lens package for containment of an intraocular lens, the package comprising:
   a. a base;
   b. a configured cavity affixed to the upper surface of said base including a centrally located lens cavity for the support of an intraocular lens wherein said lens cavity includes a plurality of support posts, said support posts including beveled radiused support seats, said support posts being positioned vertically on a central configured rim wherein said lens cavity includes said central configured rim and a segmented disc supported by two or more semi-tubular struts, wherein said semi-tubular struts and said segemented disc extends inwardly from the inner radius of a circular support member to support said central configured rim, wherein a raised annular rim including ramped catches is positioned about said circular support member to form said lens cavity; and, c. a lens retainer cap including a gripping rim, a circular support member extending inwardly from the lower portion of said gripping rim to form an inner circular edge, an annular ring extending downwardly from said inner circular edge, a plurality of flanges extending downwardly and outwardly from the lower surface of said annular ring, said flanges bearing locking teeth upon an upper surface, a conical member located centrally within said annular ring, and a hole located centrally within said conical member wherein said lens retainer cap rotationally secures over and about said configured cavity and lens cavity for securement of an intraocular lens within said lens cavity.

2. The intraocular lens package of claim 1 wherein said beveled and radiused support seats position below said support post tops to support an intraocular lens in said lens cavity.

3. The intraocular lens package of claim 1 wherein said support posts limit downward travel of the conical member in said cap to provide for a close tolerance fit chamber.

4. The intraocular lens package of claim 1 wherein said segmented disc is ramped and slopes inwardly towards the center and inwardly towards said lens cavity for accommodation of posterior chamber intraocular lens loops.

5. The intraocular lens package of claim 1 wherein the conical member in the cap extends downwardly and inwardly toward said center hole for accommodation of posterior lens loops.

6. The intraocular lens package of claim 1 wherein spacing is provided for placement of a loop or loops between said support posts to limit rotational movement of an IOL within said lens cavity.

7. The intraocular lens package of claim 1 wherein said raised annular rim is not ramped to accommodate an intraocular lens with non-vaulted loops.

* * * * *